US011439217B2

(12) United States Patent
Drozdowska

(10) Patent No.: US 11,439,217 B2
(45) Date of Patent: Sep. 13, 2022

(54) NAIL-DECORATING AND STYLING KIT

(71) Applicant: Magdalena Drozdowska, Warsaw (PL)

(72) Inventor: Magdalena Drozdowska, Warsaw (PL)

(*) Notice: Subject to any disclaimer, the term of this patent is extended or adjusted under 35 U.S.C. 154(b) by 0 days.

(21) Appl. No.: 17/363,904

(22) Filed: Jun. 30, 2021

(65) Prior Publication Data
US 2021/0321740 A1 Oct. 21, 2021

Related U.S. Application Data

(63) Continuation of application No. PCT/PL2020/050002, filed on Jan. 9, 2020.

(30) Foreign Application Priority Data

Jan. 10, 2019 (PL) .......................... 428553

(51) Int. Cl.
A45D 29/00 (2006.01)
A61K 8/02 (2006.01)
A61K 8/42 (2006.01)
A61K 8/81 (2006.01)
A61Q 3/02 (2006.01)

(52) U.S. Cl.
CPC .......... *A45D 29/001* (2013.01); *A61K 8/0233* (2013.01); *A61K 8/42* (2013.01); *A61K 8/8123* (2013.01); *A61K 8/8147* (2013.01); *A61K 2800/88* (2013.01); *A61Q 3/02* (2013.01)

(58) Field of Classification Search
None
See application file for complete search history.

(56) References Cited

U.S. PATENT DOCUMENTS 5,415,903 A 5/1995 Hoffman et al.
6,328,949 B1 12/2001 Tessarolo et al.
(Continued)

FOREIGN PATENT DOCUMENTS

EP 3275334 A1 * 1/2018 ............. B41M 5/00
PL 168252 B1 1/1996

OTHER PUBLICATIONS

International Search Report issued by the European Patent Office for corresponding International Patent Application No. PCT/PL2020/050002, dated Apr. 2, 2020.
(Continued)

*Primary Examiner* — Nicole P Babson
(74) *Attorney, Agent, or Firm* — Myers Wolin, LLC

(57) ABSTRACT

A kit for decorating and styling nails or for supplying the substance to the nail plate comprises a foil placed on a base layer, wherein the foil optionally, on one arbitrary surface, has an decorative or single-colour overprint made directly on this surface and a self-adhesive coating on the internal side. The foil together with the self-adhesive coating and the base layer has at least eight different protrusions forming permanently formed flexible three-dimensional nail stickers, formed together with the base layer on the matrix, wherein the protrusions mirror the anatomic nail shape and moreover the foil layer together with the self-adhesive coating is cut around the perimeter of each of the protrusions. There is also disclosed a three-dimensional nail sticker for decorating and styling nails or for supplying the substance to the nail plate.

23 Claims, 7 Drawing Sheets

(56) References Cited

U.S. PATENT DOCUMENTS

| | | |
|---|---|---|
| 2005/0236100 A1 | 10/2005 | Arisawa |
| 2010/0047301 A1* | 2/2010 | Park .................... A61K 8/9794 424/401 |
| 2013/0032163 A1 | 2/2013 | Roescheisen |

OTHER PUBLICATIONS

International Preliminary Report on Patentability issued for corresponding International Patent Application No. PCT/PL2020/050002, dated Apr. 1, 2021.

* cited by examiner

NAIL-DECORATING AND STYLING KIT

CROSS-REFERENCE TO RELATED APPLICATIONS

This application is a continuation of International Application PCT/PL2020/050002, filed Jan. 9, 2020, which claims priority to Polish Patent Application P.428553, filed Jan. 10, 2019, the contents of each of which are incorporated by reference herein.

FIELD

The subject of the invention is nails decorating and styling kit including self-adhesive stickers with an overprint. The invention also relates to three-dimensional nail sticker for decorating and styling nails.

BACKGROUND

There are many known methods for decorating nails and the most common is application of a nail polish. Nail extending tips are also very frequent technique of styling. These are rigid overlays of plastic that imitate nails. The tips are very precisely permanently adhered to a free edge of nails. They are matched to natural nails based on their colour and may be coated with a transparent material. Before modelling, length and shape of tips are determined which allows for optimum application of a hardening material, e.g. acrylic. Tips correct irregularities of structure and shape of a natural nail. Tips are also used to extend the nails. However, tips due to their rigidity are very susceptible to breaking off from the nail plate or breaking during frontal hit. Moreover, application of tips requires a skill set and specialized equipment. Additionally, the tips themselves and their removal negatively affect the nail plate condition.

It is a common method to decorate the nail plate using flat stickers. There are resin-based stickers with solvents, water stickers, so-called decal, stickers applied using a heat or vinyl stickers. Flat stickers are adhered to a surface and after their removal they are applied onto the nail plate. Flat stickers, as opposed to the tips, are not formed to fit the anatomical shape of a nail. Therefore, after adhering the nails, they tend to unstick at the edges which fact translates to short durability and unaesthetic appearance. Moreover, a flat resin-based sticker with solvents is stretched over the nail plate matching its surface to the convex surface of a nail. Admittedly, resin based stickers are very elastic, however their application requires some skill set. Moreover, in case of the resin-based stickers with solvents, it is necessary to use them within one day after opening a blister, because the solvents evaporate from the sticker and therefore the unused stickers dry out and become brittle and useless. Because of their brittleness, resin-based stickers tend to chip off at the edges. Additionally, the stickers have an unpleasant smell and their frequent application leads to deterioration of the nail plate. Water stickers are however rather thin and delicate, which fact hinders their application on nails. Alike the aforementioned stickers—water stickers are flat and must be adapted to the nail plate surface. Stickers applied using heat are another type of flat stickers. They can be characterized by rigidity which fact strengthens the sticker, however at the same time it necessitates application of heat using a hair dryer or dedicated lamp—in order to become more flexible and susceptible to shaping on a nail plate. These stickers are difficult to apply and file at the edges. Moreover, they necessitate application of a heat source, such as dedicated lamp or hair dryer. Additionally, they tend to wrinkle thus return to flat form and unstick from a nail resulting in poor durability. Similar situation is in case of vinyl stickers designed for application without the need to apply heat. They can be characterized by better flexibility than stickers applied with heat, however they are much more delicate and less durable. They also tend to return to their flat, initial form, to deform, wrinkle on a nail, and therefore to unstick from the nail. Moreover, their application requires some skill set.

The American patent application U.S. Pat. No. 5,415,903A discloses self-adhesive laminate on fingers and nails. The laminate consists of a layer of film-forming polymer comprising at least one plasticizer, self-adhesive layer placed on it and carrying foil that covers the pressure-sensitive adhesive layer and that can be removed again. The film-forming layer is also covered from the other side, at least on a part of its surface with a protective layer that can also be removed and is resistant to other components of the laminate and materials used for its preparation. The invention also applies to a method of production of such laminate and its application onto toe nails. The laminate according to the above patent application is a flat product susceptible to unsticking.

The American patent application US 20130032163A1 discloses a system and method of applying a foil onto nails. The foil application method includes cleaning the nail surface, applying the first layer of nail polish, adhering the nail foil and sealing the nail foil by applying the second layer of nail polish onto the nail foil. The patent application describes flat stickers.

Moreover, Polish patent application PL 168252 discloses a method of decorating nails and a tool to decorate the nails. The method of decorating nails consists in that width of thermoplastic, coloured, adhesive foil strips of plastic is adapted to the size of a nail, paper that secures the foil against adhering is removed and such foil strips are heated with hot air until they gain suitable plasticity and then they are pressed to the nails and formed according to the nail shape with simultaneous adhering the heated foil to the nail. Then, the flow of hot air is cut off and after cooling the foil down, its edges are cut to the nail size. A special device for decorating nails is used for that purpose. This solution provides durable results however it is labour- and time-consuming and requires major skill set. Moreover, because it is necessary to cut foil strips from a larger sheet, it is only possible to use one-colour foil without a chance to obtain repeatable decorative pattern.

Moreover, American patent application U.S. Pat. No. 6,328,949B1 discloses a nail covering system that consists in scanning a nail of a person in order to prepare a digitized image of the top surface of the nail and to shape the covering material so that the material covering the nails matches the nail top, creating a dimensioned nail cover. The aforementioned procedure can be used in beauty parlours and cannot be performed at home. The aforementioned procedure leads to only a two-dimensional, flat projection of the upper surface of the nail plate.

The nail stickers have numerous, aforementioned drawbacks.

SUMMARY

Three-dimensional nail stickers according to the invention eliminate such drawbacks and provide a completely new quality product. The object of the invention is development of three-dimensional nail stickers that do not tend to deform and return to flat form, that do not unstick after adhering to the nail plate, that do not necessitate application of heat or specialist tool and skill set The object of the invention is a kit for decorating and styling the nails that include foil, preferably thermoplastic, of thickness 30 to 140 μm, placed on a base layer. The foil has a self-adhesive coating from the base layer side. The foil with self-adhesive coating and the base layer has at least eight different protrusions forming permanently formed, elastic, three-dimensional nail stickers, formed together with a base layer on a matrix, however the protrusions mirror the anatomic nail shape. The permanently formed protrusions created in the foil with self-adhesive coating, forming the nail stickers, imitate anatomic, three-dimensional form of nail plates. Shape of the nail plate is individual for each person and can differentiate with both the plate width and its roundness therefore in order to satisfy the needs of as many users as possible, the kit for a single hand or foot has at least 8 pieces of protrusions. The foil layer together with self-adhesive coating is cut around the perimeter of each protrusion and allows for separating a single nail sticker together with the self-adhesive coating from the base layer. The base layer can be made of the same material as foil. In case of thermoplastic foil and thermoplastic base layer, the protrusions are formed using heat. The forming can also be performed using mechanical methods, applying mechanical pressure during hot or cold pressing.

Preferably, the base layer is made of amorphous polyethylene terephthalate APET or high impact polystyrene HIPS or polyethylene terephthalate PET or polyethylene terephthalate glycol PETG or poly(methyl methacrylate) PMMA or acrylonitrile butadiene styrene ABS of thickness 200 μm in case of thermoforming or resin or natural rubber or rubber or silicone or paper pulp form coated with silicone.

Preferably, the foil is made of polyvinyl chloride or linear low density polyethylene (LOPE) or polyethylene terephthalate (PET) or amorphous polyethylene terephthalate (APET) or polylactic acid (PLA).

Preferably, the base layer is coated with an additional external coating from the self-adhesive side.

Preferably, the additional external coating is made of UV-hardened silicone.

Preferably, the self-adhesive coating is represented by an adhesive having an attestation for skin contact.

Preferably, the self-adhesive coating is represented by an acrylic acid copolymer.

Preferably, the self-adhesive coating includes an additive of a substance that cares for the nail plate.

Preferably, the self-adhesive coating includes ceramides and/or vitamins and/or proteins as an additive of a substance that cares for the nail plate.

Preferably, the self-adhesive coating includes a medicinally active substance, preferably a medicinally active substance selected from an antifungal substance and/or an antibacterial substance.

Preferably, two kits for nails decoration are placed on the same base layer.

Preferably, the foil has a decorative or single-colour overprint made directly on that surface on any one surface.

Preferably, the overprint is covered with a protective laminate.

Preferably, the protective laminate is polyvinyl chloride of thickness 30 μm.

Preferably, the layer of foil and self-adhesive coating is cut around the perimeter of each protrusion together with the base layer, except the flat narrow strip connecting the protrusions together.

Preferably, the layer of foil and self-adhesive coating is cut around the whole perimeter of each protrusion together with the base layer.

Preferably, the layer of foil and self-adhesive coating exists as a single protrusion chosen for application to one particular nail plate.

Preferably, the film layer and self-adhesive coating include personalized protrusions made to the individual order of a particular user.

Preferably, the film layer and self-adhesive coating include 10 personalized protrusions made to the individual order of a particular user.

Antifungal substances and/or antibacterial substances used to treat the nail plate contained in the adhesive coating can be selected from known: Ciclopiroxum, Amorolfine, Climbazole, Piroctone Olamine, Itraconazolum, Triclosan, Tea tree oil, Bifonazolum, Urea.

The advantage of using the active ingredient in the adhesive coating is ensuring the possibility of supplying the active ingredient of the drug from the sticker to the nail plate over its entire surface thanks to three-dimensional matching to the convex nail plate, also on the sides of the nail plate, which was not possible with previously known flat stickers containing active healing ingredients. The use of the sticker and an active ingredient ensures both a healing and aesthetic effect, because the infected nail layer is covered with foil. Also, the use of the sticker and covering it with e.g. nail polish, protects the nail plate from the effects of harmful components contained in the nail polish, thus accelerating the treatment effect.

The invention also relates to three-dimensional nail sticker for decorating and styling nails including sticker with self-adhesive layer placed on the base layer, wherein the three-dimensional nail sticker comprises the foil of thickness between 30 and 140 μm placed on the base layer, wherein the foil, from the base layer side, has the self-adhesive coating and the foil together with the self-adhesive coating and the base layer has protrusion forming permanently formed flexible three-dimensional nail sticker, formed together with the base layer on the matrix, wherein the protrusion mirror the anatomic nail shape and moreover the foil layer together with the self-adhesive coating is cut around the perimeter of the protrusion, wherein the base layer can be made of the same material as the foil and in case of using the thermoplastic foil and thermoplastic base layer, the protrusions are made by heat forming.

Preferably the three-dimensional nail sticker is the part of the kit according to invention.

The solution according to the invention can be used for finger and toe nails.

A kit for decorating and styling nails is provided that consists of a series of flexible stickers of formed anatomic shape eliminating drawbacks of flat stickers and tips. The same advantages has three-dimensional nail sticker according to the invention. Decorating nails with stickers according to the invention is simple, does not require any additional devices and can be performed directly by an individual, and the result is durable. The foil can be ready to use because of the overprint on one of its surfaces made directly on such surface, but it can also be transparent, without an overprint in order to allow a user to decorate it using e.g. multicolour lacquers and creating own, arbitrary compositions. The foil together with the caring additives and with or without an overprint performs at the same time a caring function. Spatially-formed sticker with the "shape memory" does not tend to deform and maintain its three-dimensional shape, anatomically adapted to the nail shape.

The result of three-dimensional forming the stickers is maintained by the formed base layer. They do not need to be stretched during application on the nails and the self-adhesive layer has an adhesive that is safe in contact with the skin, therefore it does not ruin nails. Moreover, in case of using the caring additives in the self-adhesive layer, it cares and nourishes the nail plate.

In order to use the solution according to the invention, take the kit or sticker out of the package and clean the nails by degreasing the nail plate. Then, among the available protrusions, select the one that matches best to the anatomic shape of the user nail plate. Next, remove the sticker from the base. Unstuck sticker has three-dimensional shape that mirrors the anatomic shape of the nail. Therefore, it can be used for easy application on the nail. Next, stick the sticker to the nail plate, starting from the nail lunula. It is not necessary to mechanically stretch and form the sticker foil, because the sticker formed to the anatomic nail shape adapts to the nail plate. Therefore, the sticker is adhered directly on the nail. At the last stage, file the excess of the sticker to the nail with a file to match its size to the nail length. It is also possible to make additional decoration of the sticker using a nail polish or other decorative means as well as to extend its life by applying additional preparation designed for that purpose.

The solution according to the invention provides a product that can be characterized by a shape representing anatomic shape of the nail. The shape is determined by protrusions formed on the matrix. According to the invention, flexible three-dimensional stickers are provided that can be characterized by convex, three-dimensional form that is a section of a sphere. The shape like this results in decidedly better adherence of the sticker to the nail plate comparing to the solutions according to the art throughout the whole period of the product use as well as faster and easier application, because the product does not require stretching a flat form onto a convex nail. The stickers according to the invention are much more durable than those known in the art (see the comparison of the appearance and adhesion to the nail plate of the stickers of FIGS. 10 A-C with the stickers of the invention after one week of use shown in FIG. 11 D).

Another feature resulting from the anatomic and three-dimensional stickers form is the easiness of their application on the nail plate. Sticking the stickers according to the invention does not require experience or any special technical preparations.

What's important is that their applying is an operation lasting less than in case of stickers according to the art. The self-sticking coating is represented by a special adhesive that is attested for skin contact resulting in safety and isolation of the nail plate from harmful external factors.

An important feature of the solution according to the invention is the option to correct irregularities of the structure and shape of a natural nail. The solution is designed to decorate and style the nail plate.

Stickers according to the invention can be offered in the form of a single protrusion. It allows the user to choose a specific, single shape from a wide range of sizes and shapes, including those atypical. The sticker is selected by fitting on the shape from the shape sampler in traditional sales channels, e.g., beauty salons, drugstores. The sticker can also be selected virtually using the application scanning the image of the user's hand and determining the three-dimensional shape of the nail plate based on the programmed characteristic points.

Stickers according to the invention can be made to individual order for the shapes of specific user's nail plates. It gives the possibility of even more precise covering the sticker to the nail plate while increasing the ease of application and durability of the stickers. The mapping of personalized protrusions is done by scanning the surface of the user's nail plates with a 3D scanner in traditional sales channels, e.g., beauty salons, drugstores. Mapping of personalized protrusions can also be done virtually using a mobile or computer application scanning the image of the user's hand and determining the three-dimensional shape of the nail plate based on the programmed characteristic points.

Stickers according to the invention made to individual order for the nail shapes of a user's hands or feet contain a set of 10 protrusions. The digitized three-dimensional image of nail plate shapes is stored in a user database. On request, a set of personalized stickers for hands or toes is made, taking into account the characteristic shape of the user's nail plates simultaneously covered with selected from the catalog or personalized decorative overprint.

The solution has been tested in order to determine optimum shapes of the three dimensional protrusions.

BRIEF DESCRIPTION OF DRAWINGS

The subject of the invention is presented on the figure, where.

Figure 11:
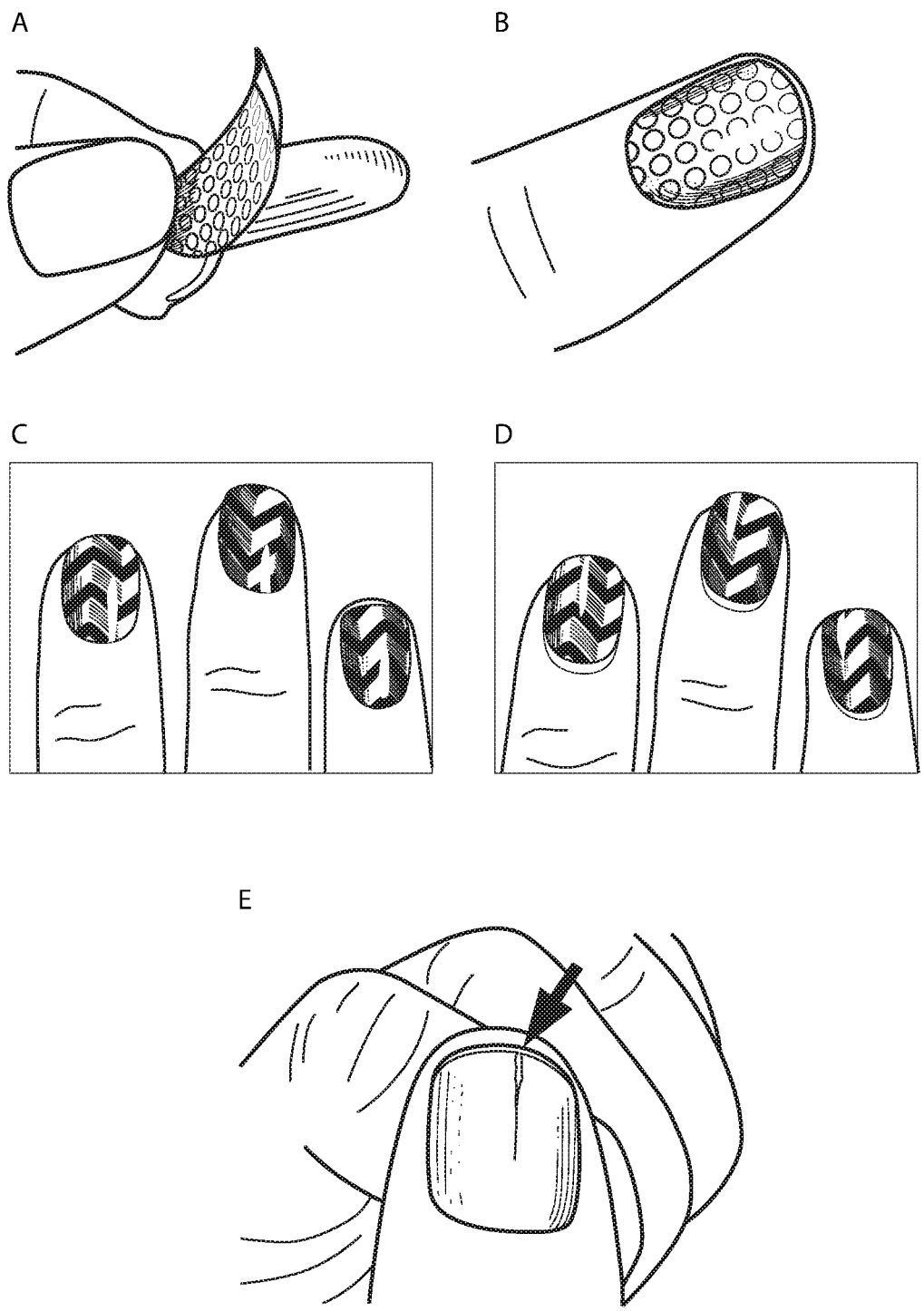

A) stickers known in the art as resin-based stickers, stuck on nails, after 3 days of use—visible unsightly chipping on the nail plate;

B) stickers known in the art intended to be applied using heat, stuck on nails, after 3 days of use—visible waving and peeling of the stickers;

C) stickers known in the art as made of vinyl, stuck on nails, after 3 days of use—visible waving and peeling of the stickers—visible waving and wrinkling of the stickers;

FIG. 11 presents the pictures of nail stickers from the kit according to the invention A) a decorative sticker from the kit according to the invention, peeled off the base layer and curled up, followed by B) sticker stuck to the nail;

C) picture of the nail stickers according to the invention immediately after applying to the nails and the same stickers D) 7 days after applying on the nails and everyday use. The stickers according to the invention show excellent adhesion over the entire surface of the nail plate, ensure the durability of use and aesthetic effect for a minimum of 7 days of use since application, they do not chip off, do not wrinkle or wave. E) a sticker according to the invention produced according to the Embodiment 7 with the active substance applied to a cracked nail (crack indicated by an arrow), protects it from further mechanical damage and provides medicinal substances in the form of an antifungal substance.

DETAILED DESCRIPTION

The following examples illustrate the invention without limiting it in any way.

Examples

Example 1. In order to make the kit for decoration and stylization of nails, first a three dimensional matrix is developed with different protrusions that mirror anatomic shapes of the nail plate. The matrix can be made of any material that can be permanently shaped in order to represent the basis for protrusions that condition correct—anatomic shape of the sticker. The matrix can be made of epoxy resin, aluminium, MDF, rubber, silicone, using the casting technology, 3D printing, injection or CNC machine forming. Then, the flat, non-formed foil of polyvinyl chloride of thickness 60 µm is printed with multicolour geometric pattern decorating the nail plate. The pattern can be any ornament, uniform colour or other decorative form. The printing is additionally coated with polyvinyl chloride of thickness 30 µm that protects the printing. Flat, non-formed and printed thermoplastic foil of polyvinyl chloride is coated at the next stage with a copolymer of acrylic acid that represents a self-adhesive coating. The adhesive has an attestation for skin contact and therefore it is harmless and practically odour-free. The adhesive has an addition of ceramides as the substances caring for the nail plate. The foil together with the self-adhesive coating is applied on the base layer made of amorphous polyethylene terephthalate APET of thickness 200 µm coated with UV hardened silicone from the self-adhesive side and applied on the matrix. The whole is subjected to heat in order to achieve noticeable softening of the used materials. The protrusions of thermoplastic foil are made using a matrix that mirrors anatomic shapes of nail plate. The matrix protrusions are permanently copied on the foil together with a self-adhesive layer and in the base layer. At the next stage, the foil is incised together with the self-adhesive layer around the perimeter of each protrusion therefore forming self-adhesive nail stickers. The stickers are still stuck to the base layer. The stickers can be cut using a punch, laser or plotter. The nail stickers kit of anatomic shape preferably includes at least 8 pieces of protrusions that allow a user for selecting proper shape and size and precise matching to individual shape of a given nail plate of one hand. Two analogical kits form a set for both hands or feet.

The kit for decorating and styling nails is provided that includes the foil 1 of polyvinyl chloride of thickness 60 µm with decorative overprint 2, additionally covered with protective laminate 3 of polyvinyl chloride of thickness 30 µm. On the other side, the foil 1 is covered with a self-adhesive coating 4 of a copolymer of acrylic acid with an addition of ceramides. The foil 1 is located on the base layer 5 of amorphous polyethylene terephthalate of thickness 200 µm, coated from the side of the self-adhesive coating 4 with an additional external coating 6 of UV hardened silicone. The foil 1 together with a self-adhesive coating 4 and the bottom base layer 5 has eight different protrusions 7 forming the nail stickers 8 formed together with the base layer 5. The foil 1 layer together with self-adhesive coating 4 has incisions 9 around the perimeter of each protrusion 7 and allows for separating a single nail sticker 8 together with the self-adhesive coating 4 from the base layer 5. The package includes two identical kits, one for each hand or foot.

Figure 1:
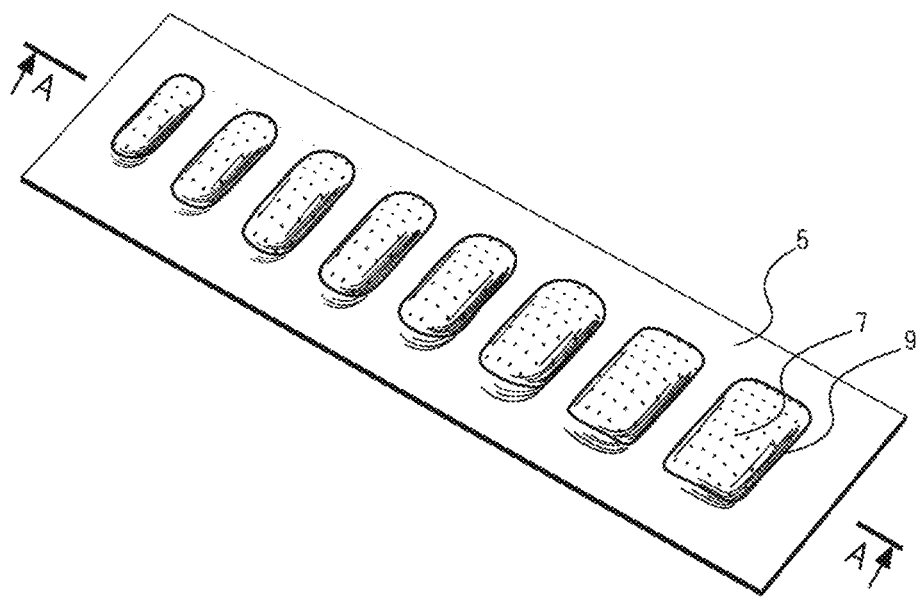
FIG. 1 presents the kit including eight stickers.
Figure 2:
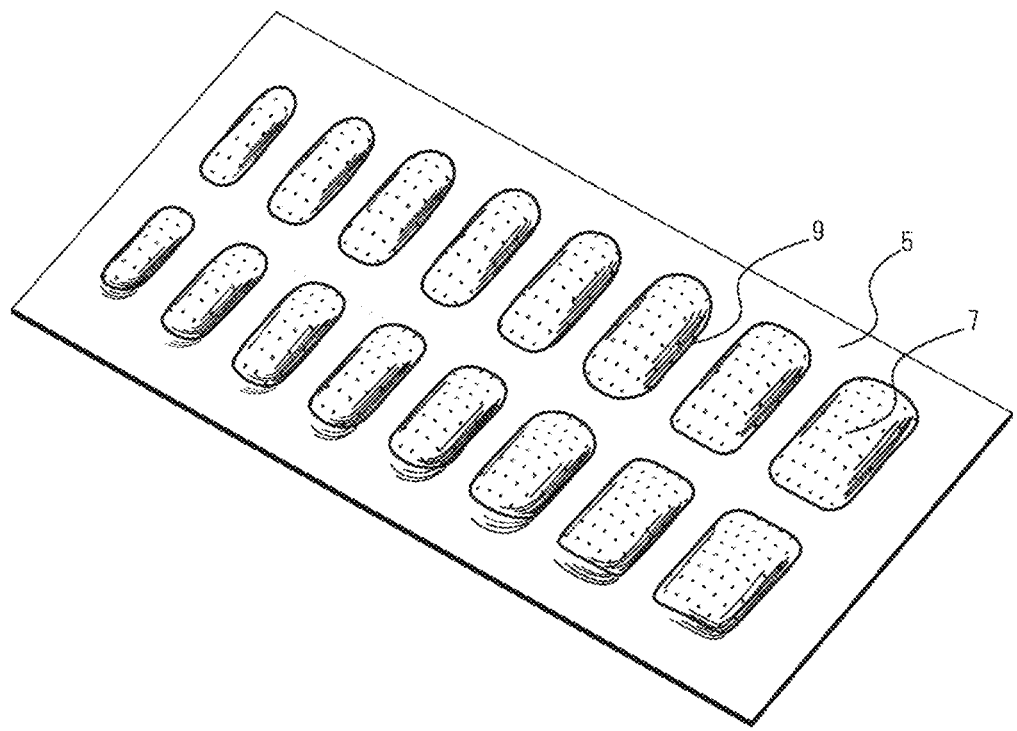
FIG. 2 presents the kit including two kits of eight stickers on a single base layer.
Figure 3:
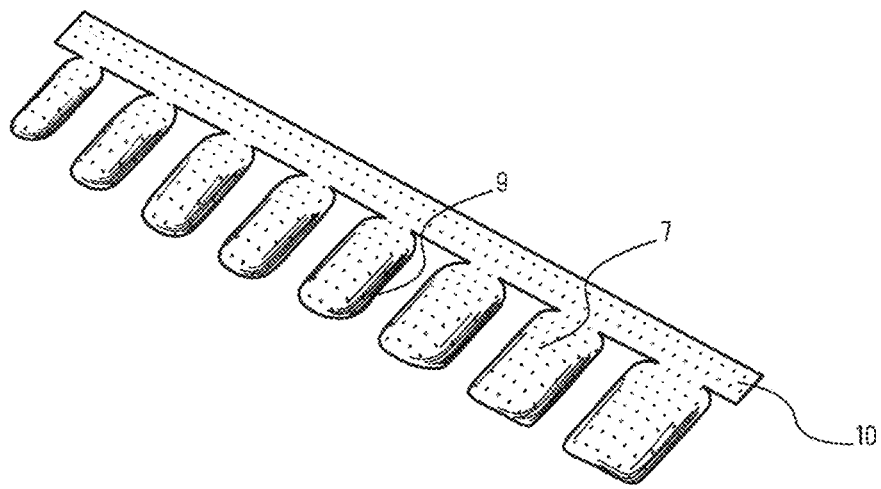
FIG. 3 presents the kit including eight stickers where the protrusions are cut together with the base layer and connected with common strip.
Figure 4:
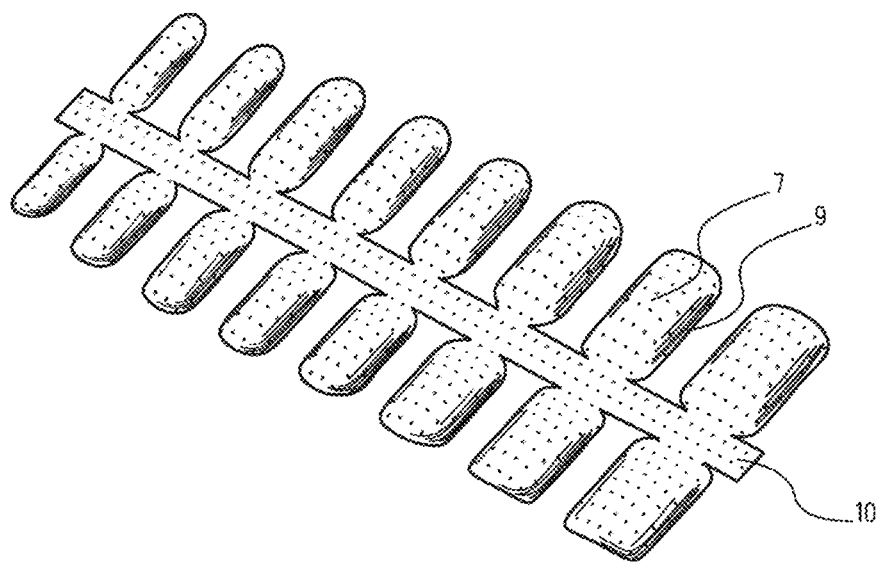
FIG. 4 presents the kit including two kits of eight stickers on a single base layer where the protrusions are cut together with the base layer and connected with common strip.
Figure 5:
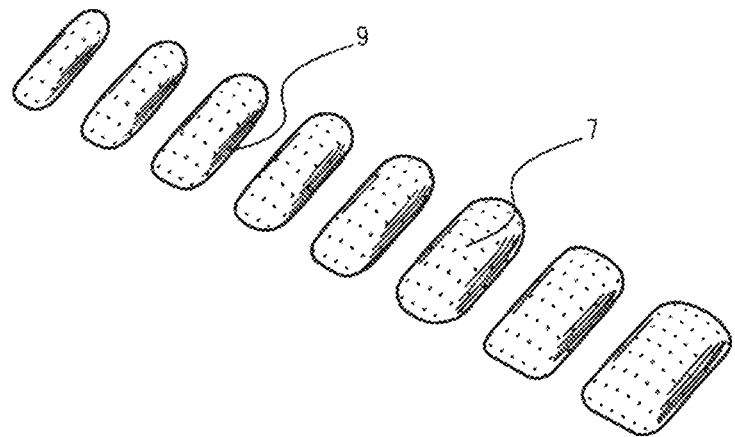
FIG. 5 presents the kit including eight stickers cut together with the base layer.
Figure 6:
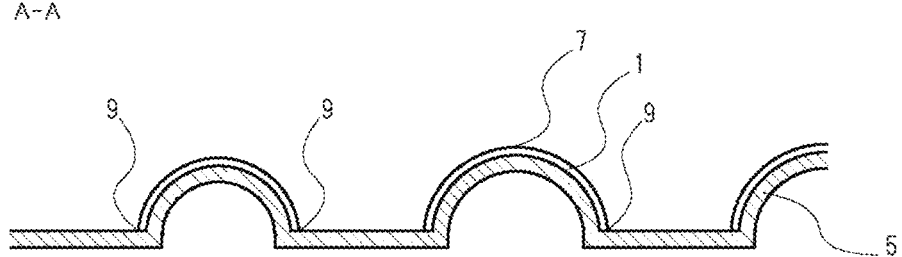
FIG. 6 presents cross-section along the line A-A, FIG. 7 schematically presents an array of layers of the kit in a variation with all the described layers.
Figure 7:
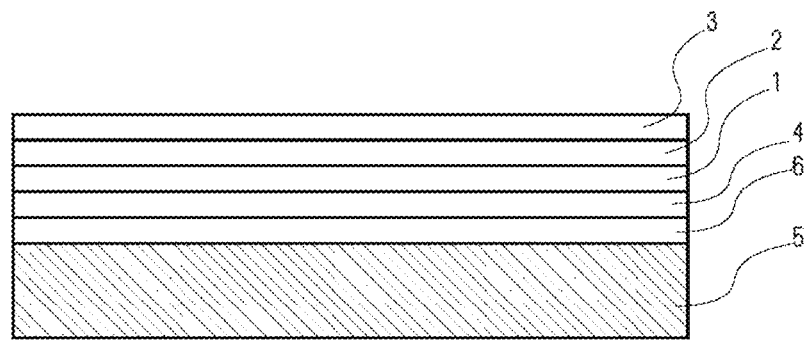
Figure 8:
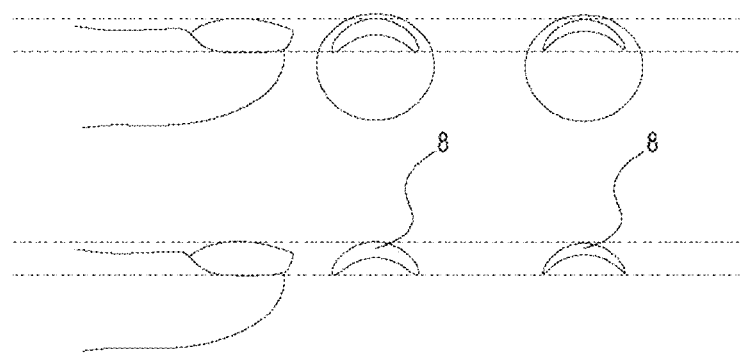
FIG. 8 presents the sticker shape comparing to the nail shape.
Figure 9:
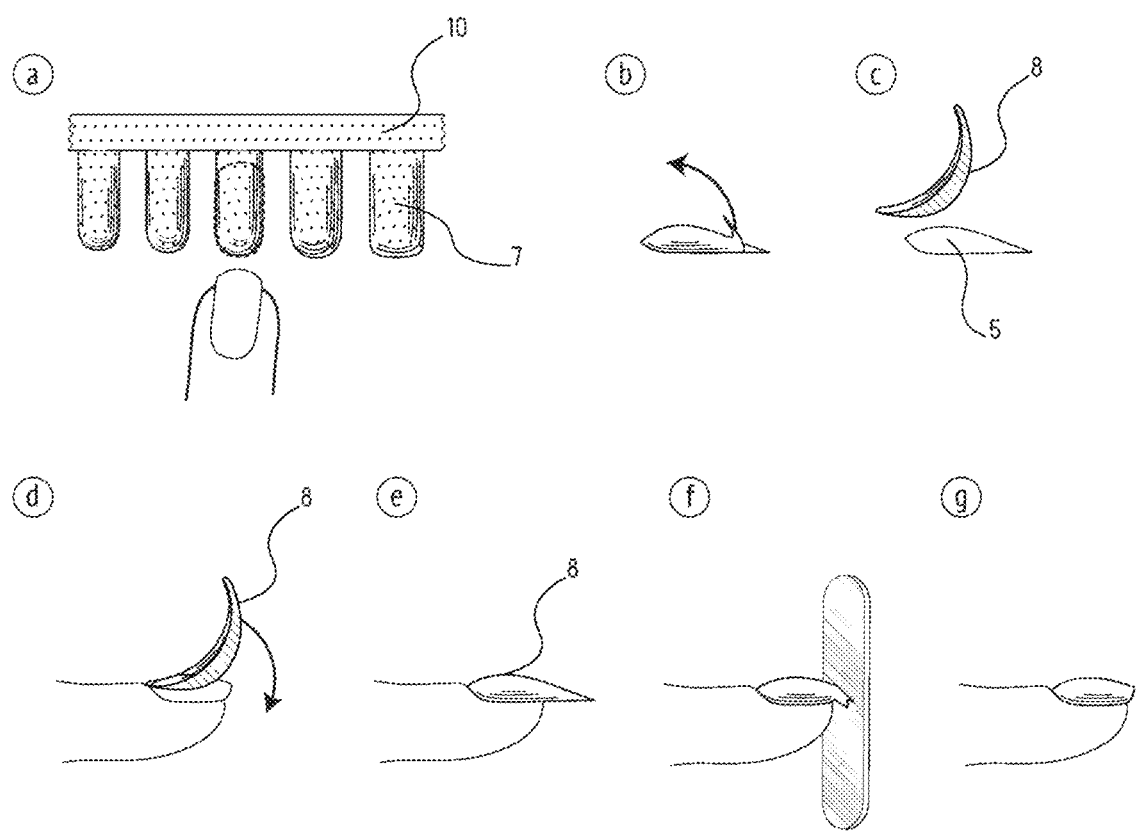
FIG. 9 presents the sticker usage stages a-g.
Figure 10:
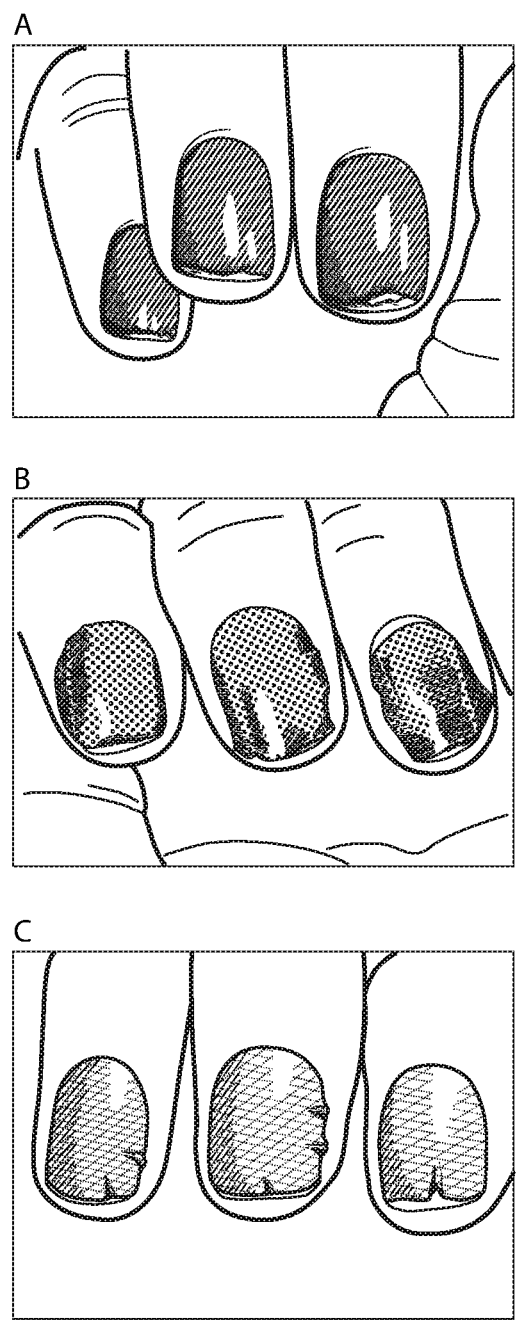
FIG. 10 presents the pictures of nail stickers known in the art

In order to use the stickers according to the invention, take the kit out of the package and clean by degreasing the nail plate. Then, among the available protrusions 7, select the one that matches best to the anatomic shape of the user's particular nail plate. Unstick the selected stickers 8 from the base layer 5. Unstuck stickers 8 curl up to the other side while maintaining their three-dimensional shape. Place the stickers 8 on the nail plate starting from the nail lunula. While applying the stickers curl back in order to restore their initial shape. The stickers are formed to the anatomic nail shape so they perfectly cover entire nail plate. File off the excess of the stickers to match their length to the nail length. The stickers 8 permanently imitate the natural shapes of the nails and do not tend to unstick. Due to their elasticity, they perfectly adapt to the nail shape. The individual stages of the method of applying stickers to the nail plate are presented on FIG. 9 a-g.

Example 2. The kit analogical as in example 1 is provided, however the same common base layer 5 has two kits 8 protrusions 7 each.

Example 3. The kit analogical as in example 1 is provided, however the protrusions 7 are cut out together with the base layer 5 leaving a flat connecting strip 10 that connects the protrusions 7 and the package includes two identical kits 8 protrusions 7 each.

Example 4. The kit analogical as in example 2 is provided, however the protrusions 7 are cut out together with the base layer 5 leaving a flat connecting strip 10 that connects the protrusions 7.

Example 5. The kit analogical as in example 1 is provided, however the protrusions 7 are cut out together with the base layer 5 and the package includes two identical kits 8 protrusions 7 each.

Example 6. Forming the stickers according to embodiments 1 to 5 can be performed using a mechanical forming method by hot or cold pressing (stamp+matrix). It is also possible to use other foil such as LOPE (linear low density polyethylene), PET (polyethylene terephthalate), APET or PLA (polylactic acid).

It is also possible to use as the base layer HIPS (high impact polystyrene), PET, PETG (PET with glycol), PMMA (poly(methyl methacrylate)), ABS (acrylonitrile butadiene styrene terpolymer), poly(acrylonitryle-co-butadiene-co-styrene), resin, natural rubber, rubber, silicone, paper pulp coated with silicone.

Example 7. The kit analogical as in example 1 is provided, however the foil 1 of polyvinyl chloride of thickness 60 µm does not include decorative overprint 2 and is not covered with protective laminate 3. On one side, the foil 1 is covered with a self-adhesive coating 4 of a copolymer of acrylic acid with an addition of Piroctone Olamine as antifungal substance.

LIST OF REFERENCES

1. Foil
2. Decorative overprint
3. Protective laminate
4. Self-adhesive coating
5. Base layer
6. External coating
7. Protrusions
8. Stickers
9. Incisions
10. Connecting strip

I claim:

1. A kit, comprising:
   a base layer; and
   at least one three-dimensional, flexible, and shape memory nail sticker placed on the base layer,
   wherein the at least one three-dimensional, flexible, and shape memory nail sticker comprises:
      a film of thickness between 30 and 140 μm, and
      a self-adhesive coating at the base layer side,
   wherein the film together with the self-adhesive coating and the base layer forms a three-dimensional protrusion,
   wherein the three-dimensional protrusion mirrors an anatomic nail shape of a whole nail plate, such that the at least one three-dimensional, flexible, and shape memory nail sticker has a protrusion shape that is convex and that is a section of a sphere, the section of the sphere mirroring the anatomic nail shape,
   wherein each of the at least one three-dimensional, flexible, and shape memory nail sticker is a permanently formed flexible three-dimensional nail sticker placed on the base layer, and each of the film and the self-adhesive coating includes an edge along a perimeter of the three-dimensional protrusion, and
   wherein when the at least one three-dimensional, flexible, and shape memory nail sticker is unstuck from the base layer and is placed on a nail layer starting from the nail lunula, the at least one three-dimensional, flexible, and shape memory nail sticker is configured to:
      curl back to restore the anatomic shape of the at least one three-dimensional, flexible, and shape memory nail sticker that is placed on the base layer, and
      maintain the anatomic shape of the at least one three-dimensional, flexible, and shape memory nail sticker that is placed on the base layer, such that the at least one three-dimensional, flexible, and shape memory nail sticker is anatomically adapted to the nail shape.

2. The kit according to claim 1, wherein the film is a thermoplastic film.

3. The kit according to claim 1, wherein the film is made of: polyvinyl chloride; linear low density polyethylene (LDPE); polyethylene terephthalate (PET); amorphous polyethylene terephthalate (APET); or polylactic acid (PLA).

4. The kit according to claim 1, wherein the self-adhesive coating includes an attestation for skin contact.

5. The kit according to claim 1, wherein the self-adhesive coating has as an additive of an active ingredient.

6. The kit according to claim 1, wherein the film has a decorative or single colour overprint on one side made directly on this surface.

7. The kit according to claim 1, wherein the film is covered with a protective laminate.

8. The kit according to claim 7, wherein the protective laminate is a polyvinyl chloride of thickness 30 μm.

9. The kit according to claim 1, wherein the base layer (5) is coated from the self-adhesive coating side with an additional external coating.

10. The kit according to claim 9, wherein the additional external coating is made of a UV-hardened silicone.

11. The kit according to claim 1, wherein the base layer is made of amorphous polyethylene terephthalate (APET); high impact polystyrene (HIPS); polyethylene terephthalate (PET); polyethylene terephthalate glycol (PETG); poly methyl methacrylate (PMMA); acrylonitrile butadiene styrene (ABS); polyvinyl chloride; polylactic acid (PLA) of thickness 200 μm in case of thermoforming; resin; natural rubber; rubber; silicone; or paper pulp form coated with silicone.

12. The kit according to claim 1, wherein the at least one three-dimensional, flexible, and shape memory nail sticker is made on a personalized protrusion shape of a specific user's nail plate, and
   wherein the three-dimensional protrusion has a shape that mirrors a three-dimensional anatomic shape of the nail of the specific user's nail plate.

13. The kit according to claim 12, wherein the personalized three-dimensional shape of the protrusion is done by scanning a surface of the user's nail plate with a 3D scanner.

14. The kit according to claim 1, wherein the at least one three-dimensional, flexible, and shape memory nail sticker comprises at least eight three-dimensional, flexible, and shape memory nail stickers, and
   wherein each of eight three-dimensional, flexible, shape memory nail stickers of the at least eight three-dimensional, flexible, and shape memory nail stickers that are placed on the base layer has a three-dimensional shape of a different protrusion that mirrors the anatomic nail shape of the whole nail plate.

15. The kit according to claim 14, wherein the kit comprises at least one set least one set of the at least eight three-dimensional, flexible, and shape memory nail stickers placed on the same base layer.

16. The kit according to claim 14, wherein the kit comprises at least two sets of the at least eight three-dimensional, flexible, and shape memory nail stickers placed on the same base layer.

17. The kit according to claim 14, wherein the edges of each of the film and the self-adhesive coating includes an edge along the perimeter of each of the protrusions, and
   wherein the film and the self-adhesive coating are not placed on a flat narrow strip of the base layer, the flat narrow strip connecting the protrusions together.

18. The kit according to claim 14, wherein the at least eight three-dimensional, flexible, and shape memory nail stickers are made on personalized three-dimensional protrusion shapes of a specific user's nail plates, and
   wherein the three-dimensional shape of the protrusions mirrors a three-dimensional anatomic shape of the nails of the specific user's nail plates.

19. The kit according to claim 18, wherein the personalized three-dimensional protrusion shapes are done by scanning surfaces of the user's nail plates with a 3D scanner and mirror nail shapes of the user's hands or feet.

20. The kit according to claim 5, wherein the active ingredient is chosen from antifungal and antibacterial substance, and wherein the active ingredient chosen from antifungal and antibacterial substance includes Ciclopiroxum; Amorolfine; Climbazole; Piroctone Olamine; Itraconazolum; Triclosan; Tea tree oil; Bifonazolum; Urea; ceramides; vitamins; and/or proteins.

21. The kit according to claim 1, wherein the base layer includes:
   a base surface; and
   a plurality of protrusions, each of the plurality of the protrusions protruding from the base surface,
   wherein the at least one three-dimensional, flexible, and shape memory nail sticker includes a plurality of three-dimensional, flexible, and shape memory nail stickers, and wherein the plurality of three-dimensional, flexible, and shape memory nail stickers are separate, and are respectively placed on the plurality of protrusions of the base layer.

22. A method of using the kit of claim 1, comprising:
unsticking one of the at least one three-dimensional, flexible, and shape memory nail sticker from the base layer,
placing the one of the at least one three-dimensional, flexible, and shape memory nail sticker on the nail plate starting from the nail lunula,
applying the one the at least one three-dimensional, flexible, and shape memory nail sticker on the whole nail plate, wherein the one of the at least one three-dimensional, flexible, and shape memory nail sticker curls back to restore its initial anatomic shape using its shape memory,
filing off the excess of the one of the at least one three-dimensional, flexible, and shape memory nail sticker.

23. The method according to claim 22, wherein the method further comprises selecting the nail sticker that matches best to the anatomic shape of the nail plate prior to the unsticking.

* * * * *